United States Patent
Mueller et al.

(10) Patent No.: US 8,022,053 B2
(45) Date of Patent: Sep. 20, 2011

(54) ORAL SOLID DOSAGE FORMS CONTAINING A LOW DOSE OF ESTRADIOL

(75) Inventors: Kristina Mueller, Berlin (DE); Torsten Wagner, Berlin (DE); Adrian Funke, Berlin (DE); Christian Zurth, Berlin (DE)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 1017 days.

(21) Appl. No.: 11/262,952

(22) Filed: Nov. 1, 2005

(65) Prior Publication Data

US 2006/0111334 A1 May 25, 2006

Related U.S. Application Data

(60) Provisional application No. 60/623,858, filed on Nov. 2, 2004.

(30) Foreign Application Priority Data

Nov. 2, 2004 (EP) .................................... 04078014

(51) Int. Cl.
*A61K 31/56* (2006.01)
(52) U.S. Cl. ...................................... 514/182
(58) Field of Classification Search ............ 514/182
See application file for complete search history.

(56) References Cited

U.S. PATENT DOCUMENTS

| | | | |
|---|---|---|---|
| 2,096,744 A | 10/1937 | Hildebrandt et al. | |
| 3,318,925 A | 5/1967 | Anner et al. | |
| 4,755,386 A | 7/1988 | Hsiao et al. | |
| 5,073,374 A | 12/1991 | McCarty | |
| 5,776,492 A | 7/1998 | Betzing et al. | |
| 5,891,867 A * | 4/1999 | Lanquetin et al. | 514/170 |
| 5,891,868 A | 4/1999 | Cummings et al. | |
| 6,030,988 A | 2/2000 | Gilis et al. | |
| 6,060,077 A * | 5/2000 | Meignant | 424/434 |
| 6,323,366 B1 | 11/2001 | Wolfe et al. | |
| 6,326,366 B1 * | 12/2001 | Potter et al. | 514/182 |
| 6,455,069 B1 | 9/2002 | Michaud et al. | |
| 6,521,253 B1 | 2/2003 | Forsman et al. | |
| 6,558,707 B1 | 5/2003 | Thosar et al. | |
| 6,653,298 B2 * | 11/2003 | Potter et al. | 514/182 |

(Continued)

FOREIGN PATENT DOCUMENTS

EP 04078014.0 11/2004

(Continued)

OTHER PUBLICATIONS

The Contraception Report, "Bioequivalence between Brand-Name and Generic OCs," Jun. 2002, 13(2), 6-8.*

(Continued)

*Primary Examiner* — San-Ming Hui
*Assistant Examiner* — Paul Zarek
(74) *Attorney, Agent, or Firm* — Millen, White, Zelano & Branigan, P.C.

(57) ABSTRACT

The present invention relates to oral solid dosage forms containing a very low dose of estradiol. The dosage forms are formulated in a manner so as to avoid degradation of the estradiol and to minimise the content of polyvinylpyrrolidone, while still achieving similar fast dissolution of the estradiol. The dosage forms are useful in preventing or treating a physical condition in a woman caused by insufficient endogenous levels of estradiol.

25 Claims, 1 Drawing Sheet

U.S. PATENT DOCUMENTS

| | | | |
|---|---|---|---|
| 6,716,453 | B1 | 4/2004 | Harden et al. |
| 6,962,908 | B2 | 11/2005 | Aloba et al. |
| 6,987,101 | B1 | 1/2006 | Nashed |
| 2002/0173487 | A1* | 11/2002 | Backenfeld et al. ............ 514/58 |
| 2003/0104058 | A1* | 6/2003 | Rudnic et al. ................ 424/468 |
| 2003/0144258 | A1* | 7/2003 | Heil et al. .................... 514/170 |
| 2003/0191103 | A1* | 10/2003 | Grubb et al. ................. 514/182 |
| 2005/0020554 | A1* | 1/2005 | Ahmed et al. ............... 514/182 |

FOREIGN PATENT DOCUMENTS

| | | |
|---|---|---|
| FR | 2 823 976 A | 10/2002 |
| RU | 2101013 C1 | 11/1996 |
| WO | WO 97/12600 A1 | 4/1997 |
| WO | WO 98/04268 * | 2/1998 |
| WO | WO 98/27929 | 7/1998 |
| WO | WO 99/26631 A1 | 6/1999 |
| WO | WO 01/52857 A1 | 7/2001 |
| WO | WO 02/47632 A1 | 6/2002 |
| WO | WO 02/49675 A1 | 6/2002 |
| WO | WO 03/055495 | 7/2003 |

OTHER PUBLICATIONS

Karalis V, Macheras P, Van Peer A, and Shah VP, "Bioavailability and bioequivalence: focus on physiological factors and variability," Pharmaceutical Research, Aug. 2008 (Epub Jun. 2008), 25(8), 1956-1962.*

Timmer CJ and Geurts TB, "Bioequivalence assessment of three different estradiol formulations in postmenopausal women in an open, randomized, single-dose, 3-way cross-over study," European Journal of Drug Metabolism and Pharmacokinetics, Jan. 3, 1999, 24(1), 47-53.*

Chaumeil JC, "Micronization: A Method of Improving the Bioavailability of Poorly Soluble Drugs," Methods and Findings in Experimental and Clinical Pharmacology, 1998, 20(3), 211-215.*

Vagifem ® product information sheet, Jul. 2003.*

Moneghini, et al.: "Studies in Dissolution Enhancement of Atenolol, Part I." International Journal of Pharmceutics 175; 1998; pp. 177-183.

Voigt, et al., "Granulometrische Erfassung Des Einflusses Von Polyvinylpyrrolidon Auf Die Loesungsgeschwindigkeit Schwerloeslicher Arzneistoffe." Wissenschaftsbereich Pharmazie 35; 1980; pp. 311-312.

"Novel Hormone Composition and Use Thereof", Summary of FR 2823796.

Loyola University Health System Article: Drospirenone/Ethinyl Estradiol (Oral) (Tablet); 2005.

NCBI Article: The Effect of a Novel Vaginal Ring Delivering Oestradiol Acetate on Climacteric Symptoms in Postmenopausal Women. Buckler H, Al-Azzawi F; UK VR Multicentre Trial Group. Department of Endocrinology, University of Manchester and Hope Hospital, Stott Lane, Salford M6 8HD, UK, 2003.

BJOG Article: An International Journal of Obstetrics & Gynaecology vol. 110 p. 753—Aug. 2003 doi 10.1111/j. 1471-0528.2003.02408.x vol. 110 Issue 8.

Estradiol Article: What is the most important information I should know about estradiol?, 2006.

Article: MedicineNet.com article: Estradiol/ethinyl Estradiol-Oral, 2005.

Article: Drug Digest, 2005.

* cited by examiner

Fig. 1

ORAL SOLID DOSAGE FORMS CONTAINING A LOW DOSE OF ESTRADIOL

This application claims the benefit of the filing date of U.S. Provisional Application Ser. No. 60/623,858 filed Nov. 2, 2004.

FIELD OF INVENTION

The present invention relates to pharmaceutical compositions, in particular oral solid dosage forms, comprising a low dose estradiol. The dosage forms of the present invention allow for good chemical stability of the estradiol during storage while still achieving a high dissolution rate of the estradiol in water.

BACKGROUND OF THE INVENTION

Pharmaceutical dosage forms containing naturally or synthetically derived steroidal hormones often contain a low dose of these active ingredients. In the present invention the dose of estradiol is significantly lower than what has so far been administered orally in the treatment of physical conditions associated with insufficient endogenous levels of estrogens in women.

According to U.S. Pat. No. 5,891,868 (Cummings et al.), the risk of bone fractures in postmenopausal women was reduced by administering transdermally about 20 µg of estradiol, or even less than about 20 µg of estradiol, per day. Transdermal administration resulted in effective serum levels in the range between 5 and 20 pg/ml, which remained within that range for an extended period of time. Cummings et al. also suggested to administer the exogenous estrogen by other suitable routes, for example by oral or parenteral administration, but Cummings et al. further stated that "the estrogen should be administered parenterally or transdermally rather than orally. The former routes of administration are preferred over oral administration because oral administration of estrogen may lead to increased levels of sex hormone binding globulin. Sex hormone binding globulin may diminish the beneficial effects of administering estrogen to postmenopausal subjects, particularly subjects exhibiting signs of osteoporosis or loss of bone mineral density". Thus, oral administration of low doses of estrogens, such as estradiol, are considered problematic for the reason mentioned by Cumming et al.

Furthermore, it is generally considered problematic to apply oral administration of a low dose of an active agent in order to ensure constant and low serum levels in an individual for an extended period of time of up to 18 to 24 hours and to achieve this in a reproducible manner within a large population of women. In particular, it is considered problematic when administering the estrogen, estradiol, which, despite the fact that it is provided in micronised form, exhibits extremely low bioavailability. Thus, the bioavailability of micronised estradiol is only about 3-5% following daily oral administration of 1 to 3 mg of estradiol. This low bioavailability is mainly attributed to an extensive metabolism in the gut and in the liver. For that reason, it is to be expected that oral administration of a lower dose of estradiol results in an even greater loss of estradiol through this extensive metabolism since the ratio of metabolic enzymes to estradiol is considerably higher. Therefore, the skilled person would not expect that the correct low dose of estradiol, giving rise to constant serum levels in the range of 5-30 pg/ml, could be successfully determined by performing linear extrapolation of known serum levels resulting from daily oral administration of 1-3 mg estradiol.

When formulating a solid oral dosage form intended for immediate release of a low dose of a highly hydrophobic active ingredient, such as estradiol, the person skilled in pharmaceutical science would consider i) increasing the disintegration of the oral dosage form into smaller fragments, ii) increasing the release of the active ingredient into the gastric fluid, and iii) increasing the dissolution rate of the active ingredient in the gastric fluid so as to prevent that the active ingredient enters the lower intestinal tract before being absorbed in the upper intestinal tract, which is the primary site of absorption for large molecules.

In order to do so, the person skilled in pharmaceutical science would, as his primary option, choose to formulate the solid dosage form using micronised material of the active ingredient to provide a high surface area. The high surface area will then allow for a rapid dissolution.

As a second option, the scientist would formulate the solid dosage form using excipients promoting disintegration in combination with excipients promoting the wetting/solubilising of the active ingredient in water or in gastric fluid. Normally, the scientist would select polyvinylpyrrolidone (PVP), which is an excipient exhibiting solubilising effect (improving the wettability), but also binding capacity making this excipient a "first choice" option, in particularly, when formulating oral solid dosage forms of highly hydrophobic drugs. The solubilising effect of polyvinylpyrrolidone is well described in the literature. For example, polyvinylpyrrolidone has been shown to improve the solubility and dissolution rate of atenolol (Moneghini et al. Int J Pharm 175; 1998; 177-183) and to increase the dissolution of prednisolone, nitrofurantoine and nitrofural considerably from gels containing 1-10% w/w of polyvinylpyrrolidone (Voigt et al. Pharmazie 35; 1980:311-312).

WO 01/52857 describes manufacturing of oral dosage forms containing 1 to 3 mg of estradiol with polyvinylpyrrolidone 25000.

However, the present inventors have found that when a lower dose of estradiol is applied in a tablet formulation similar to those described in example 1 of WO 01/52857, a significant loss of estradiol during storage is detected, i.e. the estradiol is no longer chemically stable.

Therefore, the object of the present invention is to provide stable, oral solid dosage forms containing a low dose of estradiol without compromising rapid release and dissolution of estradiol in the gastric fluid so as to achieve reliable and sufficient low serum levels of estradiol for an extended period of time of about at least 18 to 24 hours following one single administration of said dosage form to a woman.

In other words, the object of the present invention is to provide oral solid dosage forms which comprise estradiol in a low dose and, at the same time, meet the following requirements:

Immediate release of estradiol in the gastric fluid following oral administration in order for estradiol to be absorbed in a highly bioavailable manner Chemically and physically stable, in particular with respect to estradiol Reliable and sufficient absorption of estradiol so as to achieve serum levels of estradiol that constantly remains in the range between about 5 and 20 pg/ml High content uniformity Preferably, the dose of estradiol is lower than previously applied in the treatment of postmenopausal women Prior art documents describing polyvinylpyrrolidone-free pharmaceutical compositions containing estrogens in low doses are described below.

WO 02/47692 describes a vaginal tablet composition containing 10-30 µg of estradiol. The vaginal tablets disclosed in WO 02/47692 are not suitable for oral use and the skilled person will immediately realise that estradiol will be slowly released from such vaginal tablet compositions.

WO 97/12600 (equivalent to U.S. Pat. No. 6,060,077) relates to vaginal capsules containing 2.5-15 µg of 17β-estradiol. Again, such vaginal compositions are not suitable for oral administration.

U.S. Pat. No. 6,326,366 broadly describes oral dosage forms comprising a mixture of from 0.2 to 5 mg of an estrogen, such as estradiol, and isoflavone. However, in the working examples, 0.625 mg of the estrogen is administered. The oral solid dosage forms of the present do preferably not contain isoflavone.

U.S. Pat. No. 3,318,925 describes pharmaceutical compositions comprising 7α-methyl estrone and 7α-methyl estrone 3-methyl ether in an amount of 50 µg.

SUMMARY OF THE INVENTION

The present invention addresses the above-mentioned problems. Thus, in a first aspect the present invention relates to an oral solid dosage form comprising estradiol, or a hydrate, a salt or a pharmaceutically acceptable derivative thereof, in an amount therapeutically equivalent to estradiol hemihydrate in an amount of between 0.01 mg and 0.5 mg; and at least one pharmaceutically acceptable excipient, provided that when polyvinylpyrrolidone is present the weighed ratio between polyvinylpyrrolidone and estradiol is less than 10:1.

In another aspect the present invention relates to the oral solid dosage form according to the invention for use as a medicament.

When the oral solid dosage form according to the invention is administered orally to women, the resulting serum levels remain constantly low for an extended period of time and in sufficient effective levels for preventing bone fractures in women in whom the endogenous levels of estrogen has declined. Accordingly, in still another aspect the present invention relates to the use of an oral solid dosage form according to the invention for the preparation of a medicament for the prevention of loss of bone mineral density in a postmenopausal woman.

In an analogous aspect the present invention relates to the use of an oral solid dosage form according to the invention for the preparation of a medicament for treating symptoms of insufficient endogenous levels of estradiol in a woman, in particular a postmenopausal woman.

In a further aspect the present invention relates to a process for manufacturing an oral solid dosage form of estradiol, or a hydrate, a salt or a pharmaceutically acceptable derivative thereof, in a dose of 0.01 mg to 0.25 mg, comprising the steps of a) providing a powdery mixture of estradiol, or a hydrate, a salt or a pharmaceutically acceptable derivative thereof, and at least one pharmaceutically acceptable excipient;

b) granulating said powdery mixture into a granulate by adding a binder, provided that when polyvinylpyrrolidone is used, the weighed ratio between polyvinylpyrrolidone and estradiol is less than 10:1; and optionally c) mixing the resulting granulate with further pharmaceutically acceptable excipients; and d) transforming the resulting mixture into a solid dosage unit form.

Still other aspects of the present invention will be apparent from the below disclosure and from the appended claims.

DETAILED DESCRIPTION OF THE INVENTION

As mentioned above, the skilled person would, as his first option, suggest polyvinylpyrrolidone as the binder in the preparation of the solid dosage form in since this excipient also enhances the wettability of the hydrophobic active ingredient. As apparent from Example 1 herein, the surface of micronised estradiol hemihydrate is highly hydrophobic because it does practically not dissolve in water, which should be expected because of the increase in surface area. Example 1 further shows the significant effect on dissolution by adding polyvinylpyrrolidone to the micronised estradiol; Micronised estradiol rapidly dissolves regardless of the weighed ratio between estradiol and polyvinylpyrrolidone.

Quite unexpectedly, the present inventors have found that when using polyvinylpyrrolidone in the manufacturing of solid dosage forms containing a low dose of estradiol unacceptable stability problems occur (see Example 3 herein). Similar solid dosage forms containing higher doses of estradiol, such as 1, 2 or 3 mg, were stable as expected by the skilled person (see Example 4 herein).

Consequently, the skilled person might, from a pure stability aspect, consider replacing the content of polyvinylpyrrolidone with other relevant pharmaceutically acceptable ingredients. However, suitable alternatives to polyvinylpyrrolidone do not exist in the pharmaceutical art, i.e. pharmaceutically acceptable excipients possessing binding as well as solubilising effects do not exist, except for PVP. Therefore, in view of the destructive effect of PVP, the binder may be selected among those categorised as so-called "second choice" binders. The skilled person would, however, be taught away from using these less efficient binders bearing in mind that they do not possess the same excellent wettability properties as do polyvinylpyrrolidone.

Contrary to what the skilled person would have expected, the present inventors have now provided a fast release solid dosage form containing a low dose of estradiol, in which the estradiol is chemically stable and exhibits rapid dissolution in water, without applying solubilisers and even without applying super disintegrants (see Examples 2 and 5 herein).

Furthermore, as shown in Example 6 herein, one single oral administration of a tablet of the invention, either containing 100 or 190 µg of estradiol hemihydrate, to women results in serum levels of estradiol in the desired range between 5 and 20 pg/ml for an extended period of time. The data also demonstrate that even the very low dose of estradiol hemihydrate (100 µg) results in the desired levels despite the fact that this low dose was expected to be metabolised much more extensively than the higher dose of 190 µg.

The present invention is directed to oral solid dosage forms comprising, as the therapeutically active ingredient, estradiol, or a hydrate, a salt or a pharmaceutically acceptable derivative thereof, in very low dose. The dosage form exhibits the following characteristics: rapid disintegration; rapid dissolution with respect to the active ingredient; suitable bioavailability when being orally administered; serum values of the active ingredient constantly in the range of 2-30 pg/ml; such as 5-20 pg/ml; high chemical stability with respect to the active ingredient and high content of uniformity.

In the present context, the term "oral solid dosage forms" generally refers to tablets (both swallowable-only and chewable forms), capsules, granules, granules enclosed in sachets and pills. Hence, the solid dosage form of the invention may be in the form of a tablet, capsule, gelcap, granule, sachet or a pill. In a preferred embodiment of the invention, the oral solid dosage form is in the form of a tablet or a capsule, in particular in the form of a tablet.

In an interesting embodiment of the invention, the active ingredient is a pharmaceutically acceptable derivative of estradiol. The terms "pharmaceutically acceptable derivative thereof" and "pharmaceutically acceptable derivative of estradiol" refer to esters, such as sulfate esters, of estradiol; salts of estradiol and estradiol esters, such as sodium salts, e.g. sodium salts of sulfate esters; as well as other derivatives known in the art. Typically, an ester of estradiol is in the 3-position or 7-position of estradiol. Specific examples of typical esters of estradiol include estradiol valerate, estradiol acetate, estradiol propionate, estradiol enantate, estradiol undecylate, estradiol benzoate, estradiol cypionate, estradiol sulfate, estradiol sulfamate, as well as salts thereof.

The term "estradiol" is intended to mean that the estradiol may be in the form of 17-α-estradiol or 17-β-estradiol. Preferably, the estradiol is in the form of 17-β-estradiol. The term "estradiol" also covers hydrated forms of estradiol, in particular estradiol hemihydrate.

The estradiol, or a hydrate, a salt or a pharmaceutically acceptable derivate thereof, is preferably adapted in a form facilitating homogenous distribution of the estradiol throughout the composition, such as in a form having an increased surface area. Thus, the estradiol is preferably in micronised form or may be dissolved in a solvent, such as ethanol, and then sprayed onto the surface of inert carrier particles. When estradiol, or a hydrate, a salt or a pharmaceutically acceptable derivate thereof, is provided in micronised form, it has the following particle size distribution, as determined by laser diffraction: 90% of the particles have a diameter of $\leq 20$ µm, and 50% of the particles have a diameter of $\leq 10$ µm, preferably $\leq 5$ µm. It should be understood that the term "micronised" also means that the particle size distribution, as determined by laser diffraction, is such that 90% of the particles have a diameter greater than 0.1 µm, preferably 0.2 µm. The determination of particle size by laser diffraction may be carried out using Sympatec HELIOS, (dispersion) operated with a pressure of 1-4 bar.

As indicated above, the dosage form of the invention comprises a low dose of estradiol. The term "low dose" refers to the dose of estradiol in the solid dosage form and defines a dose that is lower than the daily dose so far known to be effective in the treatment of hot flushes in postmenopausal women, namely a dose lower than 1-3 mg of estradiol. Therefore, in one embodiment of the invention, the term "low dose" refers to an oral solid dosage form comprising estradiol, or a hydrate, a salt or a pharmaceutically acceptable derivate thereof, in an amount therapeutically equivalent to estradiol hemihydrate in an amount of from 0.01 mg to 0.5 mg. Preferably, the oral solid dosage form comprises estradiol, or a hydrate, a salt or a pharmaceutically acceptable derivate thereof, in an amount therapeutically equivalent to estradiol hemihydrate in an amount of from 0.05 mg to 0.4 mg, such as in an amount of from 0.05 mg to 0.3 mg, e.g. in an amount of from 0.05 mg to 0.25 mg. More preferably, the oral solid dosage form comprises estradiol, or a hydrate, a salt or a pharmaceutically acceptable derivate thereof, in an amount therapeutically equivalent to estradiol hemihydrate in an amount of from 0.1 mg and 0.2 mg, such as in an amount of from 0.15 mg to 0.2 mg. In very interesting embodiments of the invention, the oral solid dosage form comprises estradiol, or a hydrate, a salt or a pharmaceutically acceptable derivate thereof, in an amount therapeutically equivalent to estradiol hemihydrate in an amount of about 0.1 mg, about 0.11 mg, about 0.12 mg, about 0.13 mg, about 0.14 mg, about 0.15 mg, about 0.16 mg, about 0.17 mg, about 0.18 mg, about 0.19 mg or about 0.20 mg, preferably about 0.1 mg, about 0.15 mg, about 0.19 mg and about 0.2 mg. The above-mentioned dosages preferably correspond to the daily dose. In a preferred embodiment of the invention the active ingredient is estradiol hemihydrate. However, in the case anhydrous estradiol, a salt of estradiol, or a pharmaceutically acceptable derivative of estradiol, is employed, it is routine for those skilled in the art to determine pharmacologically/therapeutically equivalent dosages of such other forms of, when the effective dose of estradiol hemihydrate is known for example, the paper of Timmer and Geurts provides guidance of how equivalent doses may be determined (see "Bioequivalence assessment of three different estradiol formulations in postmenopausal women in an open, randomized, single-dose, 3-way crossover" in European Journal of Drug Metabolism and Pharmacokinetics, 24(1):47-53, 1999).

As mentioned above, the oral dosage form of the invention exhibits immediate release of the active ingredient. The wording "immediate release", "rapid release" and "fast release" are interchangeable terms, which refer to the fact that the disintegration time is short which may then enable fast dissolution of the active ingredient. The disintegration time should be less than 10 minutes, preferably less than 5 minutes, as determined according to the United States Pharmacopoeia (USP 27; chapter <701>) without using a disc. Preferably, the disintegration time should be less than 4 minutes, even more preferably less than 3 or 2 minutes.

Furthermore, the oral dosage form exhibits rapid dissolution of the estradiol, or a hydrate, a salt or a pharmaceutically acceptable derivate thereof, in water. The term "rapid dissolution" is meant to denote that more than 70% of the estradiol, or a hydrate, a salt or a pharmaceutically acceptable derivate thereof, is dissolved from the dosage form within 30 minutes after start of dissolution testing. The dissolution testing is determined according to the standard method of the United States Pharmacopoeia (USP 27; chapter <711>) using 900 ml of water temperated at 37° C. as the dissolution media, 50 rpm as the rotation speed and a dissolution apparatus equipped with paddles. Preferably, more than 80%, such as more than 90%, of the estradiol, or a hydrate, a salt or a pharmaceutically acceptable derivate thereof, is dissolved from the dosage form within 30 minutes after start of dissolution testing. The estradiol may be dissolved even faster, such that more than 70%, more than 80%, more than 85%, or more than 90% of the estradiol, or a hydrate, a salt or a pharmaceutically acceptable derivate thereof, is dissolved within 15 minutes when tested as described above.

When used herein, the term "high chemical stability" is intended to mean that at least 95% by weight of the initial amount of active ingredient, such as estradiol hemihydrate, is present in the dosage form following storage at 40° C. and 75% RH in darkness for 3 months. In a particular interesting embodiment of the invention at least 85% by weight, preferably at least 90% by weight, most preferably at least 95% by weight of the initial amount of active ingredient, such as estradiol hemihydrate, is present in the dosage form following storage at 40° C. and 75% RH in darkness for 6 months.

In a more preferred embodiment of the invention at least 85% by weight, preferably at least 90% by weight, most preferably at least 95% by weight of the initial amount of active ingredient, such as estradiol hemihydrate, is present in the dosage form following storage at 40° C. and 75% RH in darkness for 9 months. In an even more preferred embodiment of the invention at least 85% by weight, preferably at least 90% by weight, most preferably at least 95% by weight of the initial amount of active ingredient, such as estradiol hemihydrate, is present in the dosage form following storage at 40° C. and 75% RH in darkness for 12 months.

The term "high content uniformity" means that the relative standard deviation with respect to the content of the estradiol, or a hydrate, a salt or a pharmaceutically acceptable derivate thereof, in the dosage form of the invention is less than 6%, preferably less than 3%, such as less than 2%, e.g. less than 1%.

By the term "bioavailability" is meant the amount of estradiol, or a hydrate, a salt or a pharmaceutically acceptable derivate thereof, that has been absorbed into the circulating blood following oral administration and is often determined relative to the amount present in the circulating blood following intravenous (i.v.) administration of a similar amount of the same active ingredient. The bioavailability may be determined as the ratio AUC (oral administration)/AUC (i.v. administration) or the corresponding ratio of $T_{max}$, $C_{max}$ or mean residence time (MRT).

By this invention, it has been found that oral solid dosage forms containing a low dose of estradiol, or a hydrate, a salt or a pharmaceutically acceptable derivate thereof, require proper adjustment and selection of excipients in order to be chemically stable. First of all, it has been demonstrated that the amount of excipients, which have decomposing, such as oxidising, potentials greater than or similar to polyvinylpyrrolidone, should be excluded or minimised in amounts. Accordingly, interesting embodiments of the invention encompass compositions/oral solid dosage forms in which the polyvinylpyrrolidone is excluded or is present in substantially low amounts. For example, the content of polyvinylpyrrolidone is limited to the extent that the weighed ratio between polyvinylpyrrolidone and estradiol, or a hydrate, a salt or a pharmaceutically acceptable derivate thereof, is 10:1 or less. Preferably, the weighed ratio between polyvinylpyrrolidone and estradiol, or a hydrate, a salt or a pharmaceutically acceptable derivate thereof, is less than 7:1, such as less than 5:1, e.g. less than 2:1. In a particular preferred embodiment, the dosage form according to the invention does not contain polyvinylpyrrolidone. Stated differently, the amount of estradiol, or a hydrate, a salt or a pharmaceutically acceptable derivate thereof, constitutes at least 10% by weight of the amount of polyvinylpyrrolidone, preferably at least 15%, such as at least 25%, e.g. at least 50%, more preferably at least 75%, such as at least 100%, e.g. at least 200% by weight of the amount of polyvinylpyrrolidone.

By the term "polyvinylpyrrolidone" is meant a synthetic polymer having the empirical formula $(C_6H_9NO)_n$ and a molecular weight ranging from 2,500 to 3,000,000 and which consists essentially of linear 1-vinyl-2-pyrrolidone groups. Obviously, other excipients having the same oxidising power as polyvinylpyrrolidone with respect to estradiol, or a hydrate, a salt or a pharmaceutically acceptable derivate thereof, is to be excluded or used in limited amount in the dosage forms of the invention. An example of such other exipient may be Crospovidone. When used in an oral solid dosage form, polyvinylpyrrolidone has a diversity of functions, such as acting as a disintegrant, as a dissolution aid (solubiliser, improvement of the wettability), as a suspending agent and as a tablet binder. Polyvinylpyrrolidone is, in particular, used in connection with highly hydrophobic drugs so as to overcome the critical step of solubilising the active drug in the gastric fluid before the actual dissolution can take place.

By this invention, it has been found that solubilisers, such as polyvinylpyrrolidone, must be replaced by other excipients that do not have decomposing, such as oxidising, potentials greater than that of polyvinylpyrrolidone, but that retain the high dissolution rate of the estradiol.

Therefore, in interesting embodiments of the invention, polyvinylpyrrolidone is replaced by so-called "second choice" binders.

The term "binder" as used herein is generally meant to describe an agent that imparts cohesive qualities to the powdered material(s), thus linking primary particles of powdered materials to secondary aggregates. When manufacturing tablets using a process implying directly compressing a powdery mixture of the active ingredient into tablets, a binder is added to the powder mixture so as to increase the cohesion within the tablet during the compression steps. Accordingly, the binder is said to be included in the "external phase". Conversely, when manufacturing dosage forms wherein the active ingredient is combined with excipients in a granulate, i.e., wherein the manufacturing process implies a granulation step, the binder may be added to the granulation mixture so as to stabilise the resulting granules. Then, the binder is said to be present in the "internal phase". The binder may also be added after completion of the granulation step, which relate to the binder in the "external phase". Thus, it is to be understood that the term "internal phase" refers to the composition inside the granules and the term "external phase" refers to the composition outside the granules. In some interesting embodiments of the invention, the binder is preferably in the "internal phase". When wishing to have the binder in the "internal phase", the skilled artisan knows that the binder can optionally be added as a dry powder to the mixture of powdered materials. Another option is to dissolve or suspend the binder in water or any other suitable solvent or mixture of solvents including aqueous solutions, which is then used as granulation liquid. Still another option is to add the binder partly as a dry powder to the powder mixture and partly in dissolved or suspended form via the granulation liquid.

The term "first choice binder" encompasses a binder that act as a binder (in dry as well as in wetted, swelled and dissolved form) and which also has solubilising properties. Polyvinylpyrrolidone is the sole example of such a binder. The term "second choice binder" encompasses binders that act as a binder, in dry, wetted, swelled or dissolved form in the preparation of oral dosage form. They are characterised by lacking or having limited wettability properties. That is to say that upon contacting an estrogen, such as micronised estradiol, with a media (such as an aqueous solution) comprising a "second choice binder", the contact angle between the media and the estrogen is not effectively decreased or is not decreased at all. Furthermore, such a binder does not increase the dissolution rate of micronised estradiol. Commonly used binders include acacia; alginic acid; alkali metal alginate; carbomer; dextrin; dicalcium phosphate; gelatin; glucose; guar gum; hydrogenated vegetable oil; magnesium aluminium silicate; spray-congealed mannitol; zein; starch, such as maize starch, potato starch, rice starch, tapioca starch or wheat starch; partly or fully modified or pregelatinized starch; starch derivatives, such as maltodextrin; partly or fully modified or pregelatinized starch; cellulose, such as microcrystalline cellulose; cellulose derivatives, such as carboxymethylcellulose, ethyl cellulose, hydroxypropyl cellulose, hydroxyethylmethyl cellulose, hydroxypropylmethyl cellulose and methylcellulose; and mixtures thereof.

By "starch" is generally meant a substance having the empirical formula $(C_6H_{10}O_5)_n$, where n is 300-1000 and the molecular weight is of 50,000-160,000 and which consists of amylose and amylopectin, that are both polysaccharides based on α-glucose units. Starch is derived from plant materials, and is commonly found in the form of tiny microscopic granules (5-25 microns in diameter) comprised of stratified layers of starch molecules formed around a hilum nucleus. The starch granule may be round, oval or angular in shape, and consists of a radially oriented crystalline aggregate of two anhydrous D-glucose polymers: Amylose and amylopectin. The former is a straight chain polymer of several hundred glucose units linked by alpha-1-4-glycosidic linkages. Amylopectin is a branched polymer of several thousand glucose units with alpha-1-6-glycosidic linkages at the branched points and alpha-1-4 linkages in the linear regions. Individual branches may have between 20-30 glucose residues.

In specific embodiments of the invention the starch is selected from the starches that has a content of amylose in the range of 10% and 40% by weight. Typical examples are maize starch, potato starch, rice starch, tapioca starch and wheat starch.

In one embodiment of the invention, starch is used as a binder in a concentration of 1-5% by weight of the tablet core, preferably in the range of 2-3% by weight, such as about 2.5% (w/w). The starch may be used in swelled, suspended or dissolved form in a granulation liquid or in the form of dry powder. Starch may be used in its unmodified, modified as well as partially modified form. When used herein for the purpose of granulating a powdery mixture of estradoil and at least one pharmaceutically acceptable excipient, the starch is preferably in the unmodified form. As will be understood from the examples provided herein, the total amount of starch may, however, be significantly higher than indicated above, e.g. in the range of 5-25% by weight of the tablet core.

The terms "modified starch" and "pregelatinized starch" are interchangeable terms and are meant to define starch that has been chemically and/or mechanically processed to rupture all or part of the granules in the presence of water and subsequently dried. Some types of pregelatinized starch may be modified to render them improved compressibility and flowability character. Typically pregelatinized starch contains 5% of free amylose, 15% of free amylopectin and 80% unmodified starch. Pregelatinized starch may be maize starch that is processed in the above-described chemical and/or mechanical manner. Other types of starch than maize starch may be pregelatinized, such as rice or potato starch.

The terms "partially modified starch" and "pregelatinized starch" are interchangeable terms and are meant to define a pregelatinized starch that is modified to a lower extent than pregelatinized starch. Pharmaceutical grades of fully pregelatinized starch use no additives and are prepared by spreading an aqueous suspension of ungelatinized starch on hot drums where gelatinization and subsequent drying takes place. Subjecting moistened starch to mechanical pressure produces partially pregelatinized starch.

The term "unmodified starch" is meant to define unprocessed starch as defined under the term "starch" above.

The term "cellulose derivatives" is meant to encompass cellulose in which a portion, or all, of the free hydroxy groups have been replaced by ether- and/or ester groups. Thus, a cellulose derivative is a cellulose ether and/or a cellulose ether. The ether or ester groups may have various carbon chain lengths such as chains with up to 10 carbon atoms, preferably up to 8, 6, 5, or 4 carbon atoms. Typical examples on cellulose derivatives are the carboxymethyl cellulose sodium, ethylcellulose, hydroxypropyl cellulose, hydroxypropyl methylcellulose, methylcellulose. Interesting binders are the low-substituted cellulose derivativess, especially hydroxypropyl methylcellulose and hydroxypropyl cellulose. The term "low-substituted" indicates that not less than 5% and not more than 16% of the hydroxyl groups have been replaced by an ether and/or ester group. The cellulose derivatives may be selected according to their resulting viscosity in a 2% aqueous solution. Typically, cellulose derivatives suitable as binders exhibit a resulting viscosity range in a 2% aqueous solution of 1-20 mPas, preferably of 2-12 mPas, most preferably of about 3-6 mPas. The cellulose derivative is typically used in a concentration of concentration of 0.5-5% by weight of the tablet core.

In an interesting embodiment of the invention, hydroxypropyl cellulose, such as low-substituted hydroxypropyl cellulose, is used in a concentration of 0.5-5% by weight of the tablet core, preferably in the range of 1-3% by weight, such as about 2% (w/w).

In a preferred embodiment of the invention, the binder is present in the so-called "internal phase" of a granulated mixture together with the active ingredient and optionally one or more additional pharmaceutically acceptable excipients. Thus, the binder may be suspended or dissolved in a suitable granulation liquid, which is then sprayed onto the powdery mixture of the active ingredient. Given the binder is used for the preparation of granulated matter the binder is preferably selected from unmodified starch, maltodextrin, hydroxypropyl cellulose and hydroxypropyl methylcellulose.

Thus, it should be understood that a binder, in some embodiments of the invention, is present in the internal phase only, i.e. internally and/or on the surface of the granulated form of the active ingredient. In other embodiments of the invention, the binder is present in the external phase, i.e. only outside the granules. In still other embodiments of the invention, the binder is present in the internal phase as well as in the external phase.

The oral solid dosage forms of the invention have been provided without adding a super disintegrants. Without wishing to be limited to a specific theory, the addition of super disintegrants is not necessary due to the favourable disintegration characteristics of the dosage forms according to the invention. Specific examples of super disintegrants include sodium starch glycolate, croscarmellose and crosslinked polyvinylpyrrolidone. Accordingly, in a preferred embodiment, the dosage form of the invention does not contain a super disintegrant.

The term "disintegrant" is meant to define an agent ensuring the disintegration process whereby an dosage form breaks up into fragments and particles, exposing a large surface area of the active ingredient to the gastric fluid and thus allowing dissolution to occur more rapidly. Typical examples of "normal" disintegrants are agar; alginic acid; alginates; bentonit; veegum; cellulose derivatives, such as carboxymethyl cellulose sodium; gelatine; pectines; polymethacrylic acid derivatives of starch; unmodified, modified as well as partially modified starch; polymeric sugar derivatives, such as soya polysaccharides; polymeric cyclodextrin; and xylan. A disintegrant may be present in the internal or external phase. In an interesting embodiment of the invention, the disintegrant is starch, such as a mixture of unmodified starch and modified starch.

Given that the solid dosage form is in the form of a tablet, an additional critical parameter to be considered in order to provide rapid disintegration is the tablet hardness. The compressed tablet may exhibit sufficient hardness so as to resist physical stress during packaging, transport and application. On the other hand, the hardness should allow for rapid disintegration of the tablet. Thus, in one embodiment of the invention, a hardening agent is added.

In the present context, the term "hardening agent" means an excipient that is incorporated into a compressed tablet composition to impart increased hardness thereto. Exemplary hardening agents include calcium carbonate; di- and tri-calcium phosphate; calcium sulfate; microcrystalline cellulose; powdered cellulose; dextrates; dextrin; sugars, such as dextrose, fructose, lactose, mannitol, sorbitol and sucrose; glyceryl palmitostearate; kaolin; magnesium carbonate; magnesium oxide; maltodextrin; potassium chloride, sodium chloride; starch; pregelatinized starch; talc and hydrogenated vegetable oil. In a preferred embodiment, the hardening agent is modified starch.

"Hardness" of a tablet is measured as the force in N (Newton) required to break a tablet. In an interesting embodiment, the tablet of the invention has a hardness in the range of from 25N to 120N, preferably in the range of from 35N to 90N, most preferably in the range of from 40N to 80N, corresponding to a round-shaped tablet core of about 80 mg in weight. It is well known within the skilled artisan to define suitable hardness ranges depending on the size and the shape of the tablets.

The dosage forms of the invention may comprise further additional active ingredients and/or excipients. Accordingly, in some embodiments, the dosage form further comprises one or more hormones, such as a progestin. The progestin may be selected from drospirenone, levonorgestrel, norgestrel, gestodene, dienogest, cyproterone acetate, norethisterone, norethisterone acetate, desogestrel or 3-keto-desogestrel. Preferably, such progestins are in micronised form. Preferably, the dosage form of the invention does not contain isoflavone.

Examples of further excipients include fillers (sugars, such as lactose, sucrose, dextrose and dextrates; sugar alcohols, such as mannitol, sorbitol and xylitol; carbonates and phosphates of alkaline earth metals, such as calcium carbonate and calcium phosphate; celluloses, such as powdered cellulose and microcrystalline cellulose; colloidal silica; titanium dioxide; kaolin; talc), and lubricants (such as magnesium stearate).

The tablet core may be provided with a film-coat for the ease of swallowing the tablet. The film-coating may contain film-coating agents such as hydroxypropylmethyl cellulose, macrogol, talc, and colouring agents such as titanium dioxide, ferric oxide pigment yellow.

As mentioned above, the present inventors have succeeded in preparing suitable oral solid dosage forms without applying solubilisers. Nevertheless, the dosage form of the invention may contain one or more solubiliser, such naturally occurring phosphatides, e.g. lechitin or soybean lechitin; condensation products of ethylene oxide with e.g. a fatty acid, a long chain fatty alcohol, or a partial ester derived from fatty acids and a hexitol or a hexitol anhydride, for example polyoxyethylene stearate, polyoxyethylene sorbitol monooleate, polyoxyethylene sorbitan monooleate, etc.; or salts of long-chain aliphatic phosphates, such as sodium lauryl sulphate. However, in a preferred embodiment, the dosage form of the invention does not contain a solubiliser.

As will be understood, the various embodiments described herein may be combined. Thus, in a preferred embodiment, an oral solid dosage form of the invention comprises
i) estradiol, or a hydrate, a salt or a pharmaceutically acceptable derivate thereof, in an amount therapeutically equivalent to estradiol hemihydrate in an amount of from 0.01 mg to 0.25 mg;
ii) a filler in an amount of 50-90% by weight, such as 55-85% by weight. The filler may be a sugar (typically lactose, glucose or sucrose), a sugar alcohol (typically mannitol), a starch (typically maize or potato starch) or mixtures thereof;
iii) pregelatinized (modified) starch in an amount of 6-18% by weight; and
iv) a binder in an amount of 1-5% by weight, the binder being typically starch, starch derivatives, partly or fully pregelatinized starch, cellulose, cellulose derivatives.

In a particular preferred embodiment, an oral solid dosage form of the invention comprises
i) estradiol, or a hydrate, a salt or a pharmaceutically acceptable derivate thereof, in an amount therapeutically equivalent to estradiol hemihydrate in an amount of from 0.1 mg to 0.2 mg. Most preferably, the estradiol is in the form of estradiol hemihydrate.
ii) a filler, preferably lactose monohydrate, in an amount of 50-90% by weight, such as 55-85% by weight;
iii) starch, preferably maize starch, in an amount of 10-26% by weight
iv) pregelatinized (modified) starch in an amount of 6-18% by weight; and
v) a binder, preferably hydroxypropyl cellulose, in an amount of 1-5% by weight.

As explained above, in an interesting embodiment the dosage form of the invention is in granulated form.

The phrase "granulated form" indicates that the resulting physical form, when a powdery mixture of an active ingredient and one or more excipients is transformed into partly agglomerated particles and/or granules, has a particle size larger than the unprocessed powdery mixture. The transformation may take place using any suitable apparatus known to the skilled person, preferably by contacting the powdery mixture with a granulation liquid using suitable granulation equipment, such as fluidised bed granulation.

Thus, in a further aspect the present invention relates to a process for manufacturing an oral solid dosage form of estradiol, or a hydrate, a salt or a pharmaceutically acceptable derivative thereof, in a dose of 0.01 mg to 0.25 mg, comprising the steps of
a) providing a powdery mixture of estradiol, or a hydrate, a salt or a pharmaceutically acceptable derivative thereof, and at least one pharmaceutically acceptable excipient;
b) granulating said powdery mixture into a granulate by adding a binder, provided that when polyvinylpyrrolidone is used, the weighed ratio between polyvinylpyrrolidone and estradiol is less than 10:1; and optionally
c) mixing the resulting granulate with further pharmaceutically acceptable excipients; and
d) transforming the resulting mixture into a solid dosage unit form.

By the term "granulating" is understood a mechanical process whereby a powder comprising the active component and excipients are partly agglomerated into particles and/or granules having a larger particle size than the unprocessed powder. In one embodiment, the powdery mixture of the estradiol and excipients is contacted with a granulation liquid, which may comprise the binder, swelled, partly dissolved or completely dissolved in the granulation liquid. The granulation liquid may be any suitable solvent, but generally aqueous solutions or just water are applicable. In one embodiment, the powdery mixture is contacted with the granulation liquid using suitable equipment for wet-granulation, such as fluidised bed equipment. Furthermore, high shear granulation can be used instead of fluidised bed granulation.

In another suitable embodiment of the invention, the granulation liquid does not contain the binder. The binder is then added in dry form to the powdery mixture of the estradiol concurrently with a granulation liquid.

All statements made above concerning preferred embodiments, such as preferred dosage forms, preferred binders, etc., including preferred concentrations of such excipients, apply *mutatis mutandis* to the manufacturing aspect of the present invention.

In a still further aspect, the invention relates to the use of an oral solid dosage form of the invention for the preparation of a medicament for treating or preventing a physical condition in a woman caused by insufficient endogenous levels of estrogen, such as estradiol. These conditions include, but are not limited to, osteoporosis, headaches, nausea, depression, hot flushes, decrease in bone mineral density, and increased risk or incidence of bone fracture, including vertebral and/or hip fracture. Preferably, the woman is a postmenopausal woman.

Thus, more particularly, the present invention also relates to the use of an oral solid dosage form of the invention for the preparation of a medicament for the prevention of loss of bone mineral density in a postmenopausal woman. Moreover, the present invention also relates to the use of an oral solid dosage form of the invention for the preparation of a medicament for treating symptoms of insufficient endogenous levels of estrogen, such as estradiol, in a woman.

Analogously, the present invention also relates to a method for preventing or treating a physical condition in a woman caused by insufficient endogenous levels of estrogen, such as estradiol, the method comprising orally administering an oral solid dosage form of the invention to a woman in need thereof. These conditions include, but are not limited to, osteoporosis, headaches, nausea, depression, hot flushes, decrease in bone mineral density, and increased risk or incidence of bone fracture, including vertebral and/or hip fracture. Preferably, the woman is a postmenopausal woman. Thus, more particularly, the present invention also relates to a method for prevention of loss of bone mineral density in a postmenopausal woman comprising orally administering an oral solid dosage form of the invention to a woman in need thereof. Moreover, the present invention also relates to a method for treating symptoms of insufficient endogenous levels of estrogen, such as estradiol, in a woman comprising orally administering an oral solid dosage form of the invention to a woman in need thereof.

While the present invention has mainly been discussed with reference to estradiol, or a hydrate, a salt or a pharmaceutically acceptable derivate thereof, the skilled person will understand that the principles described herein may easily be extended to also encompass other estrogens, in particular such estrogens which are sensitive to polyvinylpyrrolidone, i.e., which are chemically unstable in the presence of polyvinylpyrrolidone. Accordingly, in yet another aspect, the present invention relates to an oral solid dosage form comprising an estrogen in an amount therapeutically equivalent to estradiol hemihydrate in an amount of from 0.01 mg to 0.5 mg; and at least one pharmaceutically acceptable excipient, provided that when polyvinylpyrrolidone is present the weighed ratio between polyvinyl pyrrolidone and estradiol is less than 10:1.

The term "estrogen" is meant to encompass all compounds (natural or synthetic, steroidal or non-steroidal compounds) exhibiting estrogenic activity. Such compounds encompass natural and synthetic estradiol and its derivatives; conjugated estrogens; estrogen receptor specific agonists; and non-steroidal compounds exhibiting estrogenic activity. The term is further meant to encompass all isomeric and physical forms of the estrogens including hydrates, such as a hemihydrate; solvates; salts; and complexes, such as complexes with cyclodextrins. Preferably, the estrogen is sensitive to polyvinylpyrrolidone, i.e., the estrogen is chemically unstable in the presence of polyvinylpyrrolidone. Such estrogens may be detected by manufacturing dosage forms with and without the presence of polyvinylpyrrolidone and monitoring the chemical stability of the estrogen during storage of the dosage form over a period of about 3 months in the dark at a temperature of 40° C. and a relative humidity of 75%.

By the term "conjugated estrogen" is meant the natural conjugated estrogens, such as estrone and equilin and others obtained from pregnant mare urine. Conjugated estrogens are also made synthetically. Examples of synthetically produced estrogens include estropipate and ethinyl estradiol. Further, the term "conjugated estrogens" refers to esters of such compounds, such as the sulfate esters, salts of such compounds, such as sodium salts, and esters of the salts of such compounds, such as sodium salts of a sulfate ester, as well as other derivatives known in the art. Some specific examples include 17-α and β-dihydroequilin, equilenin, 17-α and β-dihydroequilenin, estrone, and their sodium sulfate esters.

Thus, all statements made above in connection with the aspects covering estradiol, or a hydrate, a salt or a pharmaceutically acceptable derivate thereof, apply *mutatis mutandis* to the aspect concerning estrogens. Thus, whenever the term "estradiol, or a hydrate, a salt or a pharmaceutically acceptable derivate thereof" is used in the present context, it will be understood that this term may be replaced by the term "estrogen".

The invention is further illustrated by the following non-limiting examples.

EXAMPLES

Example 1

In vitro Dissolution of Micronised Estradiol

The dissolution characteristics of micronised estradiol and mixtures of micronised estradiol and polyvinylpyrrolidone, respectively, were investigated in an in vitro dissolution test system. The dissolution tester was a USP apparatus 2 (paddle system) (See <711> of USP 27) using 900 ml of purified water temperated at 37° C. as the dissolution media and a rotation speed of 50 rpm. The estradiol and the mixtures in powdery form were placed into the dissolution vessels in an amount corresponding to 100 μg of micronised estradiol hemihydrate.

TABLE 1

Results on dissolution testing

| Powder composition | Amount of estradiol (μg) dissolved after: | | | | |
|---|---|---|---|---|---|
| | 5 min | 10 min | 20 min | 30 min | 60 min |
| 100 μg of estradiol | <3* | <3* | <3* | <3* | <3 μg* |
| 100 μg estradiol + 100 μg polyvinylpyrrolidone | 16 | 29 | 48 | 56 | 68 |
| 100 μg estradiol + 4 mg polyvinylpyrrolidone | 19 | 47 | 65 | 76 | 87 |

*means that the amount of estradiol was below the limit of quantification (3 μg)

The results demonstrate the significant influence of polyvinylpyrrolidone on the dissolution of micronised estradiol.

Example 2

Preparation of Oral Solid Dosages Form with Low Dose Estradiol

Tablet cores of 80 mg have the following composition were prepared:

| Ingredient | Amount (mg): | | |
|---|---|---|---|
| I Estradiol (hemihydrate, micronised) | 0.05 | 0.1 | 0.19 |
| II Lactose monohydrate | up to 80 mg | up to 80 mg | up to 80 mg |
| III maize starch | 14.40 | 14.40 | 14.40 |
| IV Modified starch(maize) | 9.60 | 9.60 | 9.60 |
| V maize starch | 2 | 2 | 2 |
| VI Magnesiumstearate | 0.80 | 0.80 | 0.80 |

The maize starch marked "V" may be replaced with another "second choice" binder, such as hydroxypropyl cellulose (low-substituted) in an amount of 1.6 mg The oral solid dosage forms were prepared by charging a fluidised bed granulator with ingredients I-IV (estradiol, lactose monohydrate, maize starch and modified starch), and activating the fluidised bed. An aqueous solution of ingredient V (maize starch) was then sprayed continuously onto the fluidised bed while drying by heating the air stream of the fluidised bed so as to apply 2 mg per 80 mg tablet core. At the end of the process, magnesium stearate was sucked into the granulator and mixed with the granules by maintaining the fluidised bed. Magnesium stearate may alternatively be added using a blender. The resulting granules were compressed into tablet cores by compression using a tablet press.

Example 3

Stability of Low Dose Estradiol Dosage Forms

Three different tablet formulations, A, B and C, were tested for the chemical stability of estradiol (hemihydrate form and micronised) over a period of 12 months of storage in the dark at a temperature of 40° C. and a relative humidity of 75%. The tablets were kept in closed containers during storage.

All tablet formulations (A, B and C) contained nominally 0.05 mg of micronised estradiol hemihydrate at the start of the stability study and were provided with a film-coat containing hydroxypropylmethyl cellulose, macrogol, talc, titanium dioxide and ferric oxide pigment yellow. The tablet cores of 80 mg have the following composition ("+" indicates the presence of a given component):

| Ingredient | Amount (mg) | A | B | C |
|---|---|---|---|---|
| I Estradiol (hemihydrate, micronised) | 0.05 | + | + | + |
| II Lactose monohydrate | up to 80 mg | + | + | + |
| III maize starch | 14.40 | + | + | + |
| IV Modified starch (maize) | 9.60 | + | + | + |
| V maize starch | 2 | + | | |
| V Polyvinylpyrrolidone | 4 | | + | |
| V hydroxypropylcellulose | 1.6 | | | + |
| VI Magnesium stearate | 0.80 | + | + | + |

Tablet formulation A is identical to the composition shown in Example 2 (with 0.05 mg of estradiol and 2 mg of maize starch (V)). Tablet formulations B and C are identical to tablet formulation A, with the exception that the 2 mg maize starch (ingredient V) is replaced with 4 mg of polyvinylpyrrolidone and 1.6 mg hydroxypropyl cellulose, respectively.

TABLE 2

Content of intact estradiol after storage at 40° C./75% RH

| Months | Tablet form. A | Tablet form B | Tablet form. C |
|---|---|---|---|
| 0 | 98.5% | 101.1% | 100.6% |
| 1 | 96.7% | 95.1% | 96.5% |
| 3 | 98.1% | 92.4% | 98.1% |
| 6 | 95.6% | 87.7% | 97.8% |
| 9 | 96.3% | 86.6% | 97.5% |
| 12 | 95.7% | 82.4% | 97.7% |

An amount of estradiol (%) in the range of 98–102% corresponds to 100%.

The obtained data clearly illustrate that polyvinylpyrrolidone has a destablising effect on estradiol-

Example 4

Stability of Tablet With High Content of Estradiol and Presence of Polyvinylpyrrolidone A tablet formulation, R, was tested for chemical stability of estradiol (hemihydrate form and micronised) over a period of 6 months of storage in the dark at a temperature of 40° C. and relative humidity of 75%. The tablets were kept in closed containers during storage.

Tablet formulation R contained nominally 1 mg of micronised estradiol hemihydrate at the start of the stability study. The requirement is 0.9-1.050 mg per tablet. Tablet formulation R is identical to tablet formulation B (4 mg of PVP) as described in Example 3 with the exception that tablet formulation R contains 1 mg of micronised estradiol hemihydrate.

The amount of intact estradiol was found to be 98% after storage for 1, 3 and 6 month, respectively, at 40° C. and relative humidity of 75%. These data indicate that estradiol is chemically stable when provided in tablet formulation R. The shelf-life of tablet formulation R could be estimated to about 4 years.

Example 5

Dissolution Characteristics of Low Dose Estradiol Dosage Form

The dissolution profile of tablet formulations A, B, C and D were determined by in vitro dissolution test system using USP apparatus 2 (paddle system) (See <711> of USP 27), 900 ml of purified water tempered at 37° C. as the dissolution media and a rotation speed of 50 rpm.

The tablet formulations A, B and C are as described in Example 3 and the tablet formulation D is identical to tablet formulation A with the modification that the film-coating does not contain macrogol.

TABLE 3

Results on dissolution testing

| | Amount of estradiol (%) dissolved after: | | | | |
|---|---|---|---|---|---|
| Tablet | 10 min | 20 min | 30 min | 45 min | 60 min |
| A: maize starch 2 mg | 84.1 | 96.3 | 99.5 | 100.5 | 100.6 |
| B: polyvinylpyrrolidone 4 mg | 81.2 | 97.8 | 100.2 | 100.2 | 99.6 |
| C: hydroxypropylcellulose 1.6 mg | 82.1 | 97.8 | 100.2 | 100.2 | 101.0 |
| D: as A but with no macrogol in film-coat | 86.3 | 98.4 | 102.5 | 102.5 | 102.4 |

An amount of estradiol (%) in the range of 98–102% corresponds to 100%.

The results in Table 3 indicate that all four tablet formulations A, B, C and D exhibit the same dissolution profile in water.

Example 6

Pharmacokinetic End Points (Bioavailability) For Low Dose Estradiol Tablet Formulations A bioavailability study was conducted in order to determine the serum levels of estradiol after single administration of a tablet formulation identical to the one described in Example 2 containing 190 µg and 100 µg of micronised estradiol hemihydrate, respectively. The study design was open labelled, 3 periods, 3 treatments, cross-over design with a single administration of each treatment and two weeks' washout between each period. The study population were 24 healthy postmenopausal women, age 55-75. Fasted condition was held.

Figure 1:
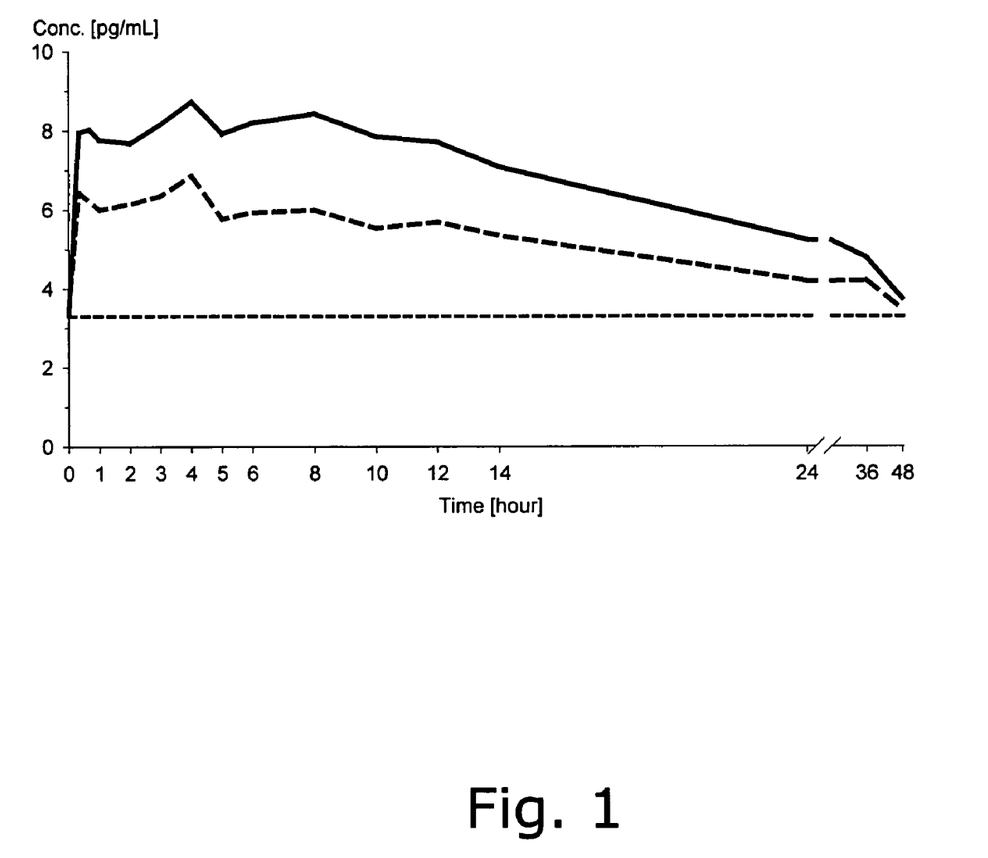
FIG. 1 shows the mean serum levels of estradiol (pg/ml) over a period of up to 48 hours. The Y-axis indicates the serum concentration of estradiol in pg/ml and the X-axis indicates the time (in hours) following administration of a single dose of estradiol. The full-drawn line and the dotted line show the serum profile following orally administering a single dose of estradiol hemihydrate of 190 µg and 100 µg, respectively. The mean serum level of endogenous estradiol (baseline) was 3-3.5 pg/ml.

FIG. 1 shows the mean serum levels of estradiol (pg/ml) over a period of up to 48 hours. The full-drawn line refers to the mean serum levels of estradiol achieved by administering a single dose of 190 µg to the study population, and the dotted line refers to the mean serum levels of estradiol achieved by administering a single dose of 100 µg to the study population. The mean serum level of endogenous estradiol was 3-3.5 pg/ml.

The results indicate that per-orally administration of 100 µg or 190 µg of micronised estradiol hemihydrate results in mean serum levels within the desired range of 5-20 pg/ml for an extended period of time.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding European application No. 04078014.0, filed Nov. 2, 2004, and U.S. Provisional Application Ser. No. 60/623,858, filed Nov. 2, 2004 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. An oral solid dosage form comprising 0.05 mg to 0.2 mg of estradiol hemihydrate, and at least one pharmaceutically acceptable excipient, provided that the dosage form does not contain polyvinylpyrrolidone, and provided that the dosage form is in a form for oral administration.

2. The dosage form according to claim 1, wherein the estradiol hemihydrate is in micronised form.

3. The dosage form according to claim 1, wherein more than 70% of the estradiol hemihydrate is dissolved from the dosage form within 30 minutes as determined by USP 27 (Paddle System) using 900 ml of water at 37° C. as the dissolution media and 50 rpm as the rotation speed.

4. The dosage form according to claim 3, wherein more than 80% of the estradiol hemihydrate is dissolved from the dosage form within 30 minutes.

5. The dosage form according to claim 4, wherein more than 90% of the estradiol hemihydrate is dissolved from the dosage form within 30 minutes.

6. The dosage form according to claim 1, wherein more than 70% of the estradiol hemihydrate is dissolved from the dosage form within 15 minutes as determined by USP 27 (Paddle System) using 900 ml of water at 37° C. as the dissolution media and 50 rpm as the rotation speed.

7. The dosage form according to claim 6, wherein more than 80% of the estradiol hemihydrate is dissolved from the dosage form within 15 minutes.

8. The dosage form according to claim 1, wherein the oral solid dosage form comprises estradiol hemihydrate in an amount of from 0.1 mg to 0.2 mg.

9. The dosage form according to claim 8, wherein the oral solid dosage form comprises estradiol hemihydrate in an amount of from 0.15 mg to 0.2 mg.

10. The dosage form according to claim 9, wherein the oral solid dosage form comprises estradiol hemihydrate in an amount of 0.2 mg.

11. The dosage form according to claim 9, wherein the oral solid dosage form comprises estradiol hemihydrate in an amount of about 0.19 mg.

12. The dosage form according to claim 9, wherein the oral solid dosage form comprises estradiol hemihydrate in an amount of about 0.15 mg.

13. The dosage form according to claim 8, wherein the oral solid dosage form comprises estradiol hemihydrate in an amount of about 0.1 mg.

14. The dosage form according to claim 1, wherein at least 95% by weight of the initial amount of the estradiol hemihydrate is present in the dosage form following storage at 40° C. and 75% relative humidity (RH) in darkness for 3 months.

15. The dosage form according to claim 1, wherein at least 85% by weight of the initial amount of the estradiol hemihydrate is present in the dosage form following storage at 40° C. and 75% relative humidity (RH) in darkness for 12 months.

16. The dosage form according to claim 1, wherein the at least one pharmaceutically acceptable excipient is a binder selected from the group consisting of starch, starch derivatives, partly or fully modified or pregelatinized starch, cellulose, cellulose derivatives, and mixtures thereof.

17. The dosage form according to claim 16, wherein the binder is a cellulose derivative is selected from the group consisting of carboxymethylcellulose, ethyl cellulose, hydroxypropyl cellulose, hydroxyethylmethyl cellulose, hydroxypropylmethyl cellulose and methylcellulose.

18. The dosage form according to claim 17, wherein the cellulose derivative is hydroxypropyl cellulose.

19. The dosage form according to claim 1, wherein the dosage form does not contain an isoflavone.

20. The dosage form according to claim 1, wherein the dosage form does not contain a solubiliser.

21. The dosage form according to claim 1, wherein the dosage form does not contain a super disintegrant.

22. The dosage form according to claim 1, wherein the dosage form is in the form of a tablet, capsule, gelcap, granule, sachet or a pill.

23. The dosage form according to claim 22, wherein the dosage form is in the form of a tablet.

24. The dosage form according to claim 23, wherein the tablet is film-coated.

25. A process for manufacturing an oral solid dosage form of claim 1, comprising the steps of
   a) providing a powdery mixture of estradiol hemihydrate;
   b) granulating said powdery mixture into a granulate by adding a binder; and optionally
   c) mixing the resulting granulate with further pharmaceutically acceptable excipients; and
   d) transforming the resulting mixture into a solid dosage unit form.

* * * * *